(12) United States Patent
Shin

(10) Patent No.: US 11,204,348 B2
(45) Date of Patent: Dec. 21, 2021

(54) MICROFLUIDIC DEVICE FOR DETECTING TARGET GENE

(71) Applicant: Korea University Research and Business Foundation, Seoul (KR)

(72) Inventor: Se-Hyun Shin, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 558 days.

(21) Appl. No.: 16/087,763

(22) PCT Filed: Feb. 16, 2017

(86) PCT No.: PCT/KR2017/001694
§ 371 (c)(1),
(2) Date: Sep. 24, 2018

(87) PCT Pub. No.: WO2017/164514
PCT Pub. Date: Sep. 28, 2017

(65) Prior Publication Data
US 2019/0113507 A1 Apr. 18, 2019

(30) Foreign Application Priority Data
Mar. 24, 2016 (KR) .................. 10-2016-0035182

(51) Int. Cl.
*G01N 33/543* (2006.01)
*G01N 33/569* (2006.01)
(Continued)

(52) U.S. Cl.
CPC ............ *G01N 33/543* (2013.01); *B01L 3/022* (2013.01); *B01L 3/502746* (2013.01);
(Continued)

(58) Field of Classification Search
None
See application file for complete search history.

(56) References Cited

U.S. PATENT DOCUMENTS

| | | | |
|---|---|---|---|
| 2002/0110495 A1* | 8/2002 | Hunt | B01J 20/281 422/400 |
| 2005/0019951 A1* | 1/2005 | Gjerde | B01J 20/285 436/177 |

(Continued)

FOREIGN PATENT DOCUMENTS

KR 10-2013-0066293 A 6/2013

OTHER PUBLICATIONS

Long et al., An isothermal and sensitive nucleic acids assay by target sequence recycled rolling circle amplification, 2013, Biosensors and Bioelectronics, 46, p. 102-107. (Year: 2013).*

(Continued)

*Primary Examiner* — Lore R Jarrett
(74) *Attorney, Agent, or Firm* — NSIP Law

(57) ABSTRACT

A microfluidic device for detecting a target gene according to the present invention comprises a plurality of capillary tubes which are partially immersed in a sample container containing sample solution and in which the sample solution flows by capillary phenomenon, and microbead packings arranged at one part in each capillary tube to be arranged on a flow path of the sample solution, wherein each of the microbead packings comprises: a packing tube arranged at the capillary tube so as to partially constitute the flow path of the sample solution, a plurality of microbeads contained in the packing tube and being in close contact with each other to form voids between the microbeads, and probe linkers formed on a surface of each microbead, wherein the probe linkers are configured to amplify a target gene in the sample solution by complementary bonding with the target gene, thereby detecting the target gene.

8 Claims, 5 Drawing Sheets

(51) Int. Cl.
  *G01N 35/08* (2006.01)
  *C12Q 1/6816* (2018.01)
  *B01L 3/00* (2006.01)
  *B01L 3/02* (2006.01)

(52) U.S. Cl.
  CPC ...... *B01L 3/502761* (2013.01); *C12Q 1/6816* (2013.01); *G01N 33/569* (2013.01); *G01N 35/08* (2013.01); *B01L 2300/0627* (2013.01); *B01L 2300/0681* (2013.01); *B01L 2300/0816* (2013.01); *B01L 2300/0838* (2013.01); *B01L 2300/0864* (2013.01); *B01L 2400/0406* (2013.01); *B01L 2400/049* (2013.01)

(56) References Cited

U.S. PATENT DOCUMENTS

2009/0215050 A1* 8/2009 Jenison ................ C12Q 1/6844
  435/6.18
2015/0298091 A1* 10/2015 Weitz ................ B01L 3/502776
  506/16

OTHER PUBLICATIONS

Lee, Ho Yeon, et al., "DhITACT: DNA Hydrogel Formation by Isothermal Amplification of Complementary Target in Fluidic Channels", Advanced Materials, 2015, vol. 27, pp. 3513-3517 (5 pages in English).

International Search Report dated Jun. 12, 2017, in International Application No. PCT/KR2017/001694 (2 pages in English, 2 pages in Korean).

* cited by examiner

MICROFLUIDIC DEVICE FOR DETECTING TARGET GENE

CROSS REFERENCE TO RELATED APPLICATION(S)

This application is a U.S. national stage application of International Application No. PCT/KR2017/001694 filed on Feb. 16, 2017, which claims the benefit of Korean Patent Application No. 10-2016-0035182 filed on Mar. 24, 2016, in the Korean Intellectual Property Office.

TECHNICAL FIELD

The present invention relates to a microfluidic device for detecting a target gene and in particular, to a microfluidic device for detecting a target gene using phenomenon in which a target gene is amplified such that a void formed by microbeads is blocked or a size of the void is reduced, for the detection of various pathogenic viruses by the target gene amplification.

BACKGROUND ART

Efficient amplification of target nucleic acid is a very important factor for detection of nucleic acid as well as DNA sequencing, cloning, etc. There are various methods for amplifying nucleic acid such as PCR (polymerase chain reaction), LCR (ligase chain reaction), SSR (self-sustained sequence replication), NASBA (nucleic acid sequence based amplification), and SDA (strand displacement amplification), etc.

Many of the above methods have disadvantages in that they have a relatively low accuracy of quantitative measurement and requires expensive devices and the disadvantages are particularly getting worse when it is needed to analyze more than one target simultaneously.

To make up for such disadvantages, an isothermal amplification was invented and in particular, a RCA (rolling circle amplification) method has been paid much attention to. That is, several techniques such as PCR have been used for detecting DNA so far, but these methods are disadvantageous since they are time-consuming, are not efficient and require high cost and manpower.

PCR method comprises a denaturation in which DNA is separated into single strand by heating DNA in reaction solution containing primer pairs, template, polymerase, and dNTP; an annealing in which a primer complementary to each separated DNA chain is bonded to a template by lowering temperature; and a polymerization in which new strands is polymerized by a polymerization reaction using polymerase by increasing temperature, and such an amplification increases DNA chain exponentially.

However, PCR process should have experience the above steps and thus, it inevitably incurs temperature change. Therefore, devices for PCR must have a temperature controller and a heating means. If PCR is used for the amplification of target nucleic acid in a lab-on-a-chip (LOC), etc., a temperature controller and a heater for PCR reaction is further required besides detection devices for LOC, it is disadvantageous that devices are complex and cost for the devices is increasing.

To solve the above disadvantage, several isothermal amplification methods have been suggested. LAMP (loop-mediated isothermal amplification) is one of the isothermal amplification methods and generates a multi-loop product having branches using 6 amplification primers. Such LAMP is not appropriate for an early diagnosis or a biosensor since an initial reverse transcriptase (RT) is used to detect a target RNA.

RCA method was suggested as another isothermal amplification method. Advantageously, RCA method does not require a temperature change necessary for the PCR amplification as described above and thus, it is possible to amplify a target nucleic acid in a isothermal state. Therefore, it is possible to amplify without a temperature controller in a process requiring the amplification, thereby reducing a complexity of the device and costs.

In a LRCA (linear rolling circle amplification) method, a target NDA sequence and an open circular probe are hybridized to form a complex and then an amplification target circle is generated by ligation, and thereafter, primer sequence and DNA polymerase are introduced. Amplification target circle forms a template in which a new DNA is formed, elongation is carried out from primer to be extended into continuous sequence of repeated sequence complementary to an amplification target circle, thereby generating thousands of copies of nucleic acid per an hour.

As a further developed method, ERCA (exponential RCA) method was developed. In the ERCA method, a new amplification center is provided using an additional primer sequence which bonds to a replicated sequence complementary to an amplification target circle, thereby the amplification is increased exponentially. In the ERCA method, a strand displacement method is continued, but it is limited to a method in which an initial single strand RCA product is used as a template of another DNA synthesis by using a separate single strand primer attached to the product without additional RCA.

Another method using molecular padlock probe (MPP) and rolling circle amplification (RCA) is disclosed (C. Larsson et al, Nat. Methods 2004, 1, 227). This method has several advantages and is characterized in that complementary nucleic acid is amplified in a circular MPP by the identification of target nucleic acid sequence and a high specificity. In particular, sensitivity is improved by direct coupling of RCA product without further purification. RCA reaction can be started on the surface by fixing target nucleic acid probes to a surface of material such as gold, quartz, etc. through simple chemical surface treatment.

Meanwhile, paper published by Ho Yeon Lee in 2015 'DhITACT: DNA Hydrogel Formation by Isothermal Amplification of Complementary Target in Fluidic Channels (Jun. 17, 2015, Advanced Materials, Volume 27, Issue 23, Pages 3513-3517) discloses a technique in which RCA reaction surface is provided on the bottom of the microchannel, then for two hours, a reaction with sample solution is carried out, and a single strand of DNA is elongated and self-assembly in the form of multiple dumbbells occurs, thereby DNA becomes to form a hydrogel shape and a flow in the corresponding channel is excluded.

However, techniques disclosed in the paper of Ho Yeon Lee have a disadvantage that it takes more than two hours to take a test, since RCA reaction surface should be formed on the bottom surface of the microchannel and then a tester has to wait until the entire microchannel is blocked by the amplification at the RCA reaction surface.

DISCLOSURE

Technical Problem

Accordingly, the present invention is provided to solve the above problems and an object of the present invention is to provide a microfluidic device for detection target gene which can reduce the detection time significantly, wherein for the detection of various pathogenic viruses by the detection of genes, the target gene is detected by phenomenon in which voids generated by the microbeads are blocked or a size of the voids is reduced by the amplification of the target gene.

Another object of the present invention is to provide a microfluidic device for detecting the target gene, wherein it is possible to quantitatively analyze the target gene according to the detection based on various methods.

Technical Solution

The above object is accomplished by a microfluidic device for detecting a target gene, comprising: a plurality of capillary tubes which are partially immersed in a sample container containing sample solution and in which the sample solution flows by capillary phenomenon, and microbead packings arranged at one part in each capillary tube to be arranged on a flow path of the sample solution, wherein each of the microbead packings comprises: a packing tube arranged at the capillary tube so as to partially constitute the flow path of the sample solution, a plurality of microbeads contained in the packing tube and being in close contact with each other to form voids between the microbeads, and probe linkers formed on a surface of each microbead, wherein the probe linkers are configured to amplify a target gene in the sample solution by complementary bonding with the target gene, thereby detecting the target gene, according to the present invention.

Here, an initial volume of the sample solution contained in the sample container may be set to make the sample solution reach the microbead packing through the capillary tube by capillary phenomenon, wherein the void may be blocked or a size of the void may be reduced by the amplification of the target gene induced by the complementary bonding between the target gene in the sample solution which reached the microbead packing and the probe linker, and wherein when the sample solution is further introduced into the sample container, the target gene may be detected based on at least one of whether the sample solution flows to the opposite side of the microbead packing or a final travel distance of the sample solution.

Also, the probe linkers of each microbead packing may be configured to detect different target genes.

Meanwhile, the above object may be accomplished by a microfluidic device for detecting a target gene, comprising: a sample chamber containing sample solution; a microchannel which is connected to the sample chamber and through which the sample solution flows; and a microbead packing arranged on a flow path of the sample solution in the microchannel; wherein the microbead packing comprises: a packing tube arranged at a microchannel so as to partially constitute the flow path of the sample solution, a plurality of microbeads contained in the packing tube and being in close contact with each other to form voids between the microbeads, and probe linkers formed on a surface of each microbead, wherein the probe linkers are configured to amplify a target gene in the sample solution by complementary bonding with the target gene, thereby detecting the target gene, according to another embodiment of the present invention.

Here, the void may be blocked or a size of the void may be reduced by the amplification of the target gene induced by the complementary bonding between the target gene and the probe linker, whereby a final travel distance of the sample solution, time taken for the final travel distance, and a flow rate of the sample solution are changed, and wherein the target gene may be detected by one of the final travel distance, the time taken for the final travel distance and the flow rate.

Also, the microfluidic device may further comprise a negative pressure chamber arranged on the opposite side of the sample chamber to be in fluid communication with the microchannel, the negative chamber applying negative pressure from outside to make the sample solution flow through the microchannel, wherein the void may be blocked or a size of the void may be reduced by the amplification of the target gene induced by the complementary bonding between the target gene and the probe linker, whereby the target gene is detected according to a change of the negative pressure applied by the negative pressure chamber.

Also, a diameter of the microbead may be set to have a size such that the target gene is able to pass through the void according to a type of the target gene within the range of 0.1 µm to 100 µm.

Also, the microbead packing may comprise meshes arranged respectively at both ends of the packing tube to prevent loss of the microbeads.

Also, the sample chamber, the microchannel and the microbead packing may be provided in plural, respectively to be arranged in parallel and the microbeads contained in one of the microbead packings do not have the probe linkers.

Also, the sample chamber, the microchannel and the microbead packing may be provided in plural, respectively to be arranged in parallel and the probe linkers of each microbead packing are configured to detect different target genes.

Also, the microchannel may comprise: a first flow channel connected to the sample chamber and a plurality of second flow channels diverged from the first flow channel, wherein the microbead packing may be provided in plural to be arranged in each of the second flow channels, wherein the microbeads contained in each microbead packing may have a different diameter.

Also, the probe linker may comprise a coating part coated on a surface of the microbead, a primer attached to the coating part, and a template which complementarily bonds to the primer, wherein the template may comprise a first bonding part which complementarily bonds to the target gene, a second bonding part which complementarily bonds to the primer, and a third bonding part which is complementary in the template to form a dumbbell, and wherein the first bonding part is divided and formed at both ends of the template and the second bonding part is formed between the third bonding part which are divided.

Also, the coating part may include one or more selected from a group consisting of 5-hydroxydopamine hydrochloric acid, norepinephrine, epinephrine, pyrogallolamine, DOPA(3,4-Dihydroxyphenylalanine), catechin, tannins, pyrogallol, pyrocatechol, heparin-catechol, chitosan-catechol, polyethylene glycol)-catechol, poyl(ethyleneimine)-catechol, poly(methylmethacrylate)-catechol, hyaluronic acid-catechol, polylysine-catechol, and polylysine.

Also, the primer may include one or more selected from a group consisting of thiol, amine, hydroxyl, carboxyl, isothiocyanate, NHS ester, aldehyde, epoxide, Carbonate, HOBtester, Glutaraldehyde, carbamate, imidazole carbamate, maleimide, aziridine, sulfone, vinylsulfone, hydrazine, phenyl azide, benzophenone, anthraquinone, and Diene groups, and wherein a terminal of the primer is modified.

Advantageous Effects

By the above arrangement, for the detection of various pathogenic viruses by the detection of genes, the target gene is detected by phenomenon in which voids generated by the microbeads are blocked or a size of the voids is reduced by the amplification of the target gene, thereby making it possible to provide a microfluidic device for detection target gene which can reduce the detection time significantly.

Also, it is possible to quantitatively analyze the target gene according to the detection based on various methods.

EXPLANATION OF REFERENCE NUMBER

| | |
|---|---|
| 1, 100, 100a, 100b, 100c: microfluidic device | |
| 10: capillary tube | 110: sample chamber |
| 120, 120a, 120b, 120c, 120d, 120e: negative pressure chamber | |
| 130: microchannel | 131: first flow channel |
| 132a, 132b, 132c, 132d, 132e: second flow channel | |
| 30, 140, 140a, 140b, 140c, 140d, 140e: microbead packing | |
| 32, 141: microbead | 142: mesh |
| 33, 143: probe liner | 144: void |
| 31, 145: packing tube | 151: stirrer |
| 152: magnet | |

Best Mode

The present invention relates to a microfluidic device for detecting a target gene and is characterized in that it comprises: a plurality of capillary tubes which are partially immersed in a sample container containing sample solution and in which the sample solution flows by capillary phenomenon, and microbead packings arranged at one part in each capillary tube to be arranged on a flow path of the sample solution, wherein each of the microbead packings comprises: a packing tube arranged at the capillary tube so as to partially constitute the flow path of the sample solution, a plurality of microbeads contained in the packing tube and being in close contact with each other to form voids between the microbeads, and probe linkers formed on a surface of each microbead, wherein the probe linkers are configured to amplify a target gene in the sample solution by complementary bonding with the target gene, thereby detecting the target gene, according to the present invention.

Mode for Invention

Hereinafter, embodiments of the present invention will be described in detail with reference to the accompanying drawings.

Figure 1:
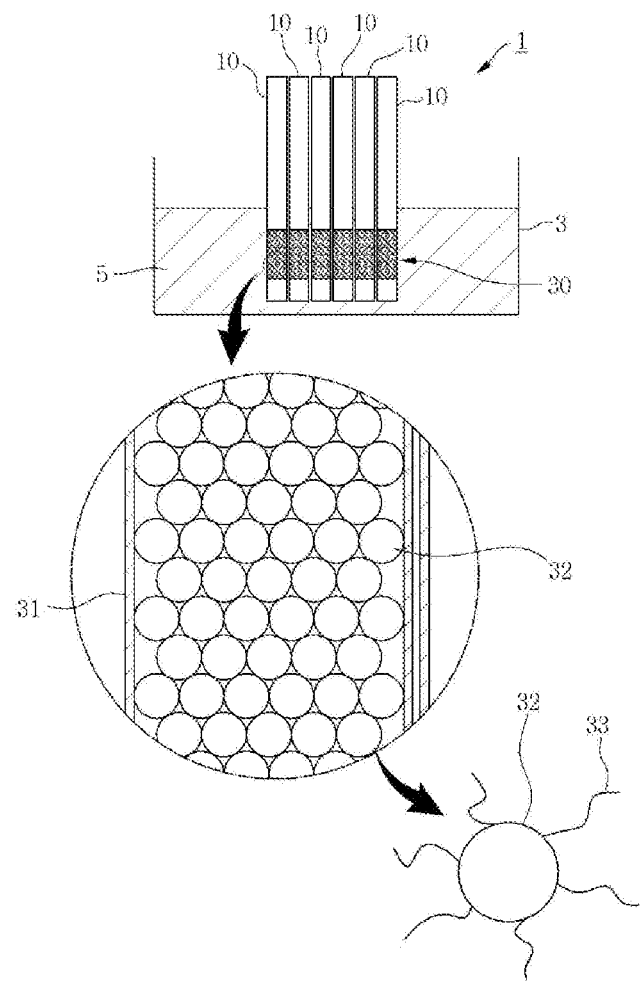
FIG. 1 is a view illustrating a microfluidic device for detecting a target gene according to one embodiment of the present invention.

FIG. 1 is a view illustrating a microfluidic device 1 for detecting target gene according to one embodiment of the present invention. Referring to FIG. 1, the microfluidic device 1 for detecting target genes according to one embodiment of the present invention comprises a plurality of capillary tubes 10 and microbead packings 30.

The plurality of capillary tubes 10 are configured to have a size such that sample solution 5 is able to flow into the capillary tube by capillarity phenomenon. In the embodiment, for example, as shown in FIG. 1, six capillary tubes are arranged to be adjacent to each other, but the arrangement of the tubes is not limited thereto.

The plurality of capillary tubes 10 are configured such that one end portion of the tube, i.e., a lower part of the tube as shown in FIG. 1, is immersed in a sample container 3 which contains the sample solution 5, and the sample solution 5 flows into the tube through an inlet at the lower side of the tube by capillarity phenomenon and flows upwards.

Microbead packing 30 is arranged in each capillary tube 10 on a flow path of the sample solution 5. Here, for example, the microbead packing 30 is manufactured separately from the microfluidic device 1 and then is inserted into the capillary tube 10 when the microfluidic device is manufactured.

Meanwhile, the microbead packing 30 according to the embodiment may comprise a packing tube 31, a plurality of microbeads 32 and probe linkers 33, as shown in FIG. 1.

The packing tube 31 is arranged on a flow path of the sample solution 5, i.e., in the capillary tube 10, to constitute some of the flow path of the sample solution 5. Also, the plurality of microbeads 32 contained in the packing tube 31 are in close and tight contact with each other and there are voids between the microbeads which are in close and tight contact with each other.

Here, a diameter of the microbead 32 depends on the type of the target gene and the size of the void varies according to a diameter of the target gene. In this regard, the size of the void is set to make the target gene pass through the void and the size of the void can be adjusted by adjusting the size of the microbeads 32. In the embodiment, for example, the diameter of the microbead 32 is determined according to the type of the target gene within the range of 0.1 μm to 100 μm.

Further, the microbead packing 30 according to the embodiment may comprise mesh 142 (see the embodiment in FIG. 4) which are arranged respectively at both ends of the packing tube 31. Advantageously, the inner diameter of the mesh 142 has a size by which the microbead 32 is not discharged and the flow of the sample solution 5 is not disturbed. Meanwhile, the probe linker 33 is formed on a surface of each microbead 32. Also, the probe linker 33 is configured such that amplification by the complementary bond with the target gene in the sample solution 5 is carried out, thereby detecting the target gene.

In the embodiment, the probe linker 33 comprises constituents disclosed in a paper 'DhITACT: DNA Hydrogel Formation by Isothermal Amplification of Complementary Target in Fluidic Channels (Jun. 17, 2015, Advanced Materials, Volume 27, Issue 23, Pages 3513-3517)' published in 2015 by Ho Yeon Lee, et al. That is, for example, the probe linker 33 comprises a coating part, a primer, and a template.

The coating part is coated on the surface of the microbead 32 and is formed of material to which the primer is attached and fixed. As described in the above paper, examples of the coating part may include one or more selected from a group of 5-hydroxydopamine hydrochloric acid, norepinephrine, epinephrine, pyrogallolamine, DOPA(3,4-Dihydroxyphenylalanine), catechin, tannins, pyrogallol, pyrocatechol, heparin-catechol, chitosan-catechol, polyethylene glycol)- catechol, poyl(ethyleneimine)-catechol, poly(methylmethacrylate)-catechol, hyaluronic acid-catechol, polylysine-catechol, and polylysine, etc.

The primer is fixed at the coating part and the template is complementarily bonded to the primer. Here, the template may comprises a first bonding part which is complementarily bonded to the target gene, a second bonding part which is complementarily bonded to the primer, and a third bonding part which is complementary in the template to form a shape of dumbbell. Further, the first bonding part is divided and formed at both ends of the template and the second bonding part is formed between the third bonding parts which are divided.

Here, examples of the primer may include one or more selected from a group consisting of thiol, amine, hydroxyl, carboxyl, isothiocyanate, NHS ester, aldehyde, epoxide, Carbonate, HOBtester, Glutaraldehyde, carbamate, imidazole carbamate, maleimide, aziridine, sulfone, vinylsulfone, hydrazine, phenyl azide, benzophenone, anthraquinone, and Diene groups, wherein a terminal is modified.

With the above arrangement, the target gene is bonded to the probe linker 33 of the embodiment and is amplified and the amplified target gene is to form hydrogel. Detailed explanation will be omitted since it is disclosed in the above paper.

As described above, an amplification by a complementary bonding of a target gene to a probe linker 33 formed on the surface of each microbead 32 generates a hydrogel, thereby blocking the void between the microbeads 32 and reducing the size of the void. The blocking of the void and the reduction of void size will be a resistance and in turn will prevent arise of the sample solution 5 due to capillary phenomenon or reduce the speed of the rise, thereby detecting a target gene.

Figure 2:
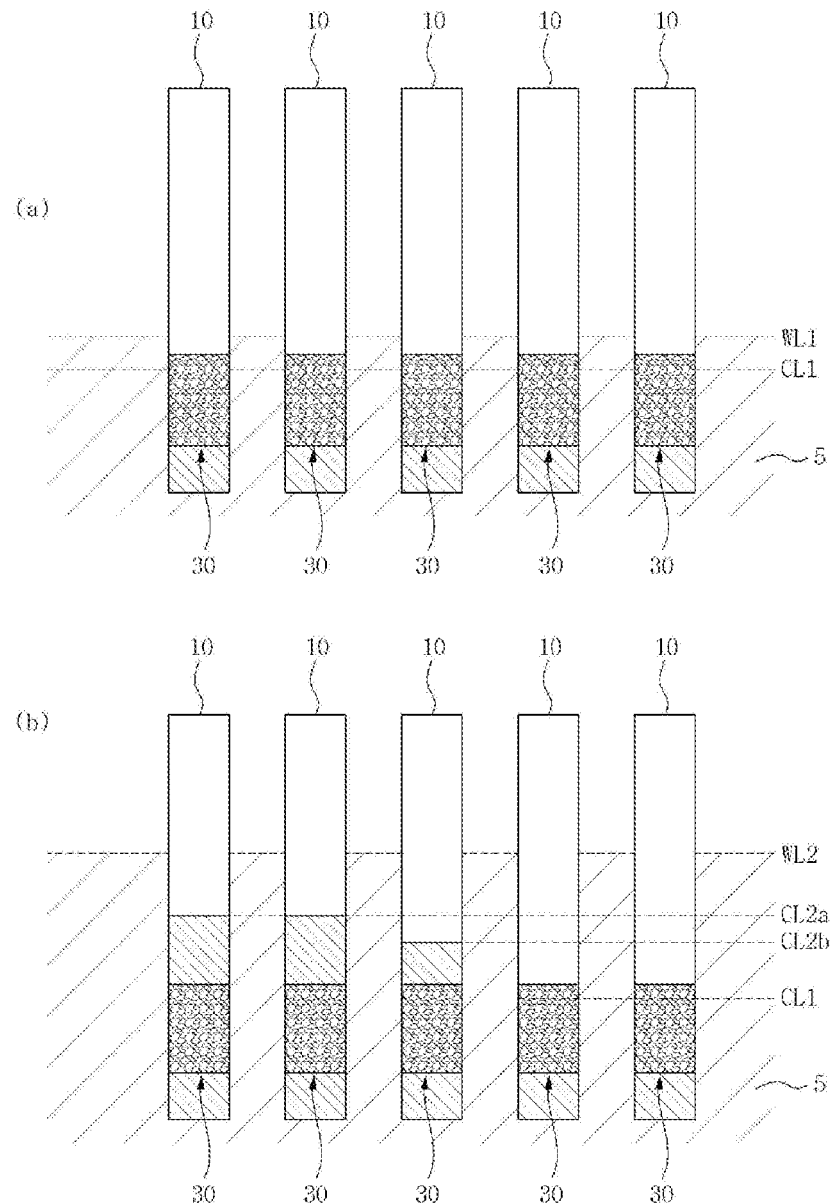
FIG. 2 is a view illustrating a method of detecting a target gene using the microfluidic device for detecting a target gene according to the embodiment.

Referring to FIG. 2, a method of detecting a target gene using the microfluidic device 1 according to the above embodiment will be described.

First, as shown in FIG. 2 (a), the sample solution 5 is poured into the sample container 3. Here, an initial quantity (WL1) of the sample solution 5 injected into the sample container 3 will be set to make the sample solution 5 reach the microbead packing 30 through the capillary tube 10 by capillary phenomenon (see CL1).

Here, the target gene in the sample solution 5 passing through the microbead packing 30 is amplified by the complementary bonding with the probe linker 33 of the microbead packing 30 and in turn, the target gene becomes hydrogel, thereby blocking the void between the microbeads 32 and reducing the size of the void.

Here, in case that probe linkers 33 of each microbead packing 30 are provided to detect different target genes, only the void of the microbead packing 30 having the corresponding target gene will be blocked or a size of the void of the microbead packing 30 having the corresponding target gene will be reduced.

Then, as shown in FIG. 2, when the sample solution 5 is further supplied into the sample container 3 (see WL2), the sample solution 5 is supposed to flow upwards through the capillary tube 10. Here, if the sample solution 5 cannot flow to reach the opposite side of the microbead packing 30 by the amplification of the target gene, the presence of the corresponding target gene can be identified.

Referring to FIG. 2 (b), in the two capillary tube 10 on the left, it can be seen that the sample solution 5 passed through the microbead packing 30 and rose (see CL2a) and this shows that the sample solution 5 has no target gene which bonds with the probe linker 33 of the microbead packing 30.

On the contrary, in the two capillary tube 10 on the right, it can be seen that the sample solution 5 did not pass through the microbead packing 30 since the microbead packing 30 is blocked and this shows that the sample solution 5 has target gene which bonds with the probe linker 33 of the microbead packing 30. And, in the capillary tube on the center, it can be seen that the sample solution 5 has relatively small quantity of target gene since the void was not blocked completely or it takes time for the void to be blocked.

In the above embodiment, it was tested whether the void is blocked by adding sample solution. In an alternative method, the capillary tube 10 is immersed in the sample solution, and then, the capillary tube 10 is immersed deeper in the sample solution after a period of certain time, for example, time for which target gene can be amplified enough. By this, if the sample solution 5 flowing upwards through the capillary tube 10 cannot flow to reach the opposite side of the microbead packing 30 due to the amplification of the target gene, it is possible to identify the presence of the target gene.

Here, in order to facilitate a visual identification as to whether the sample solution has moved to the upper part of the capillary tube 10, the color of the sample solution can be controlled. For example, a paper whose color changes when it is wet is arranged at the upper part of the microbead packing 30 in the capillary tube 10. By this arrangement, if color of the paper located in the capillary tube 10 is changed when the paper is wet by the sample solution, it can be identified that there is no target gene in the capillary tube 10.

Hereinafter, referring to FIGS. 3 and 4, the microfluidic device 100 for detecting target gene according to another embodiment will be described in detail.

Figure 3:
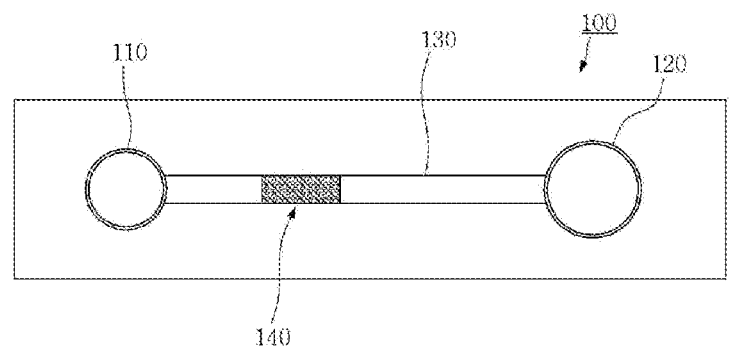
FIG. 3 is a view illustrating a microfluidic device for detecting a target gene according to one embodiment of the present invention.
Figure 4:
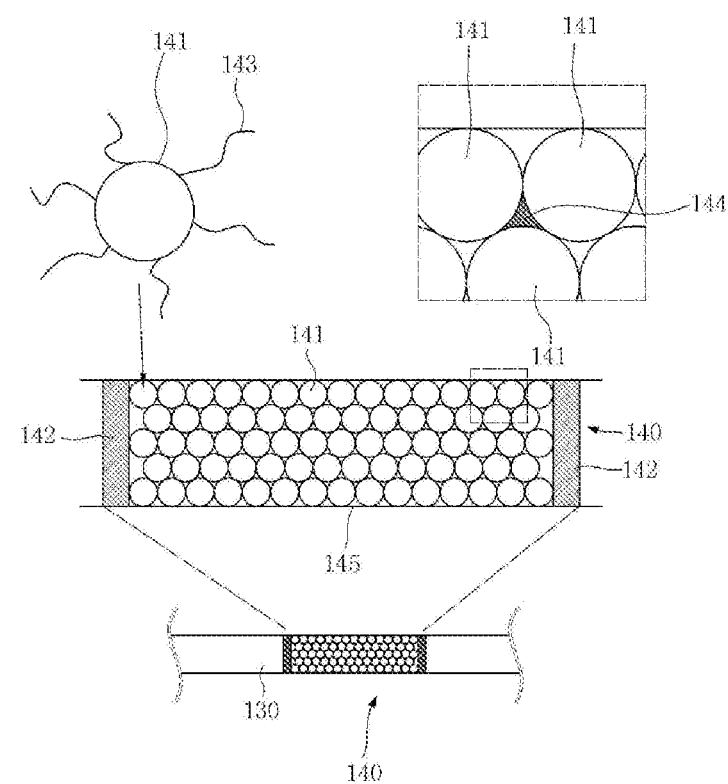
FIG. 4 is a view illustrating a microbead packing of a microfluidic device for detecting a target gene according to the embodiment of the present invention.

Referring to FIGS. 3 and 4, the microfluidic device 100 for detecting target gene according to another embodiment (hereinafter referred to as 'microfluidic device 100') may comprise a microchannel 130 and a microbead packing 140. Also, the microfluidic device 100 according to the embodiment may comprise a negative pressure chamber 120.

The sample chamber 110 is arranged at one side of the microfluidic device 100 and contains sample solution. The microchannel 130 is in fluid communication with the sample chamber 110, and the sample solution contained in the sample chamber 110 flows through the microchannel 130.

The microbead packing 140 is arranged on a flow path of the sample solution. Here, the microbead packing is manufactured separately from the microfluidic device 100 and then is installed in the microchannel 130 when the microfluidic device 100 is manufactured. For example, when an upper substrate having a sample chamber 110, a microchannel 130, and a fluid-pressure chamber is attached to a transparent base substrate in an upward and downward direction in order to manufacture the microfluidic device 100, the upper substrate is attached to the base substrate in a state that the microbead packing 140 was inserted into the microchannel 130 of the upper substrate.

Meanwhile, as shown in FIG. 4, the microbead packing 140 according to the embodiment of the present invention may comprise a packing tube 145, a plurality of microbeads 141 and probe linkers 143. Here, the microbead packing 140 corresponds to that of the embodiment in FIG. 1 and detailed explanation thereof is omitted. As shown in FIG. 4, the microbead packing 140 according to the embodiment may comprise meshes 142 which are arranged on both ends of the packing tube 145 respectively to prevent the loss of the microbeads 141. Advantageously, the size of the inner diameter of the mesh 142 is set to prevent the microbeads 141 from being discharged and not to disturb the flow of the sample solution.

Here, an amplification by a complementary bonding of a target gene to probe linkers 133 formed on the surface of each microbead 141 generates a hydrogel, thereby blocking the void 144 between the microbeads 141 and reducing the size of the void 144, thereby causing changes of a final travel distance by which the sample solution flows through the microchannel 130, time taken to reach the final travel distance, and a flow rate of the sample. Further, it is possible to detect the target gene by using at least one of the final travel distance, the travel time and the flow rate.

Referring back to FIG. 3, the negative-pressure chamber 120 is arranged on the opposite side of the sample chamber 110 and is in fluid communication with the microchannel 130. Negative pressure from outside is applied by the negative-pressure chamber 120 such that sample solution flows through the microchannel 130.

Here, if the void 144 is blocked or the size of the void 144 is reduced by the amplification due to the complementary bonding of the target gene to the probe linker 143, pressure which has been being constantly applied by the negative-pressure chamber 120 will change, thereby it being possible to identify the presence of the target gene.

According to the above embodiment, a plurality of microbeads 141 constitute the microbead packing 140, and probe linkers 143 formed on the microbeads 141 bond with the target gene. Then, the target gene is amplified and hydrogel is generated during the amplification and blocks the void 144 or reduces the size of the void 144, thereby causing the changes of the final travel distance, the travel time, the flow rate and/or pressure, whose detection makes it possible to identify the presence of the target gene.

Also, it is possible to make a test by blocking or clogging the void 144 formed by the microbeads 141 instead of blocking the entire of the microchannel 130 as disclosed in the paper, thereby making it possible to reduce test time significantly. Further, it is possible to increase a reaction area by forming probe linkers 143 on the surface of each microbeads 141, instead of forming a reaction area on the bottom surface only as disclosed in the above paper, thereby making it possible to reduce test time significantly.

It is possible to detect the presence of the target gene by clogging phenomenon of the void, and it is also possible to evaluate quantitatively the target gene by using the change of the final travel distance, the travel time, the flow rate or the pressure, etc. For example, if there are a lot of target genes, the probability of reaction increases and in turn, the void 144 is blocked more quickly and the final travel distance is reduced, which can be quantified based on a statistical method, thereby making it possible to evaluate quantitatively the target gene.

Figure 5:
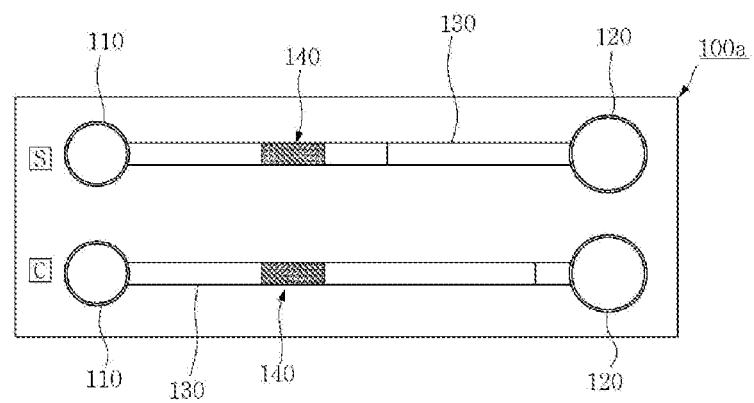
FIGS. 5 to 7 show a microfluidic device for detecting a target gene according to yet another embodiment of the present invention.

FIG. 5 shows a microfluidic device 100a according to yet another embodiment of the present invention. As shown in FIG. 5, the microfluidic device 100a according to the yet another embodiment may comprise a plurality of sample chambers 110, a plurality of microchannels 130, and a plurality of microbead packings 140. Here, the sample chamber 110 and the microchannel 130 are connected to each other by one and one to form a flow path of the sample solution and a plurality of flow paths are arranged in parallel. In FIG. 5, for example, two sample chambers 110 and two microchannels 130 are arranged in parallel to form two flow paths. The microbead packings 140 are arranged respectively in each microchannel 130.

Here, the microbeads 141 contained in one of the microbead packings 140 do not have probe linkers 143. Referring to FIG. 5, as described above, for example, the microbeads 141 of one of microbead packings 140 have probe linkers 143 and the microbeads 141 of the other of the microbead packings 140 do not have probe linkers 143.

In the example, the same sample solution is contained in each sample chamber 110 and then the sample solution flows. Here, if the microbead packing 140 has the probe linkers, the bonding and the amplification of the target gene as described above cause the microbead packing to be blocked or cause the size of the void 144 to be reduced, thereby the flow of the sample solution being restricted. On the contrary, if the microbead packing 140 has no probe linkers 143, the sample solution flowing through the microbead packing 140 flows without restriction.

Further, in case that the microbead packing 140 has the probe linkers 143, the final travel distance by which the sample solution which passed through the microbead packing 140 has traveled until the sample solution is stopped by the blocking of the microbead packing 140 is measured and the travel time thereof is measured, and then the final travel distance and time thereof are compared with those of the microbead packing 140 having no probe linkers 143, thereby it is possible to quantify an initial concentration of the target gene.

Here, in the embodiment of FIG. 5, for example, each flow path is provided with a negative pressure chamber 120. Besides, of course, it should be noted that an end of each microchannel 130 is connected to one negative pressure chamber 120, and negative pressure is applied for the flow of the sample solution by one negative pressure chamber 120.

Further, in the embodiment of FIG. 5, microbeads 141 of each microbead packing 140 may have different probe linkers 143, respectively so as to bond with different target genes. That is, since each probe linker 143 bonds with different target genes to amplify target genes, it is possible to detect a plurality of target genes simultaneously, by using one microfluidic device 100.

Figure 6:
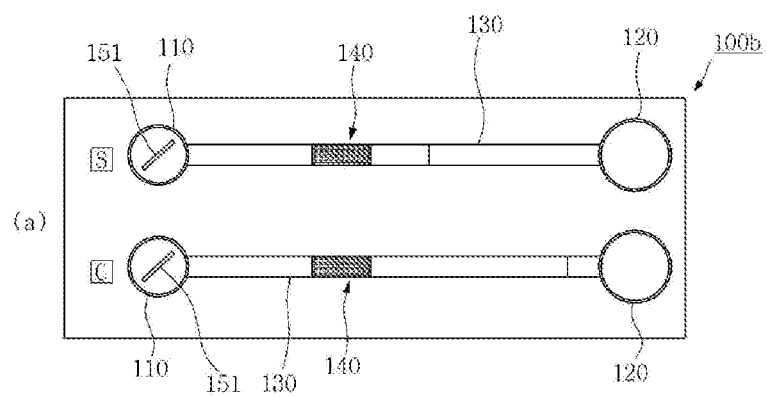
Figure 6:
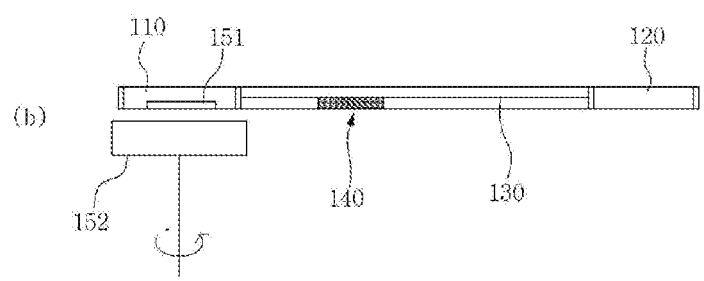

FIG. 6 shows a microfluidic device 100b according to yet another embodiment of the present invention. The embodiment as shown in FIG. 6 is a modification of the embodiment of FIG. 5 and for example, each sample chamber 110 is provided with a stirrer 151.

Here, the stirrer 151 is configured to rotate by a rotation of a magnet 152 arranged outside the microfluidic device 100. By the stirrer, the sample solution contained in the sample chamber 110 is stirred and in turn, target genes in the sample solution is distributed widely, thereby facilitating the bonding and amplification in the microbead packing 140.

Figure 7:
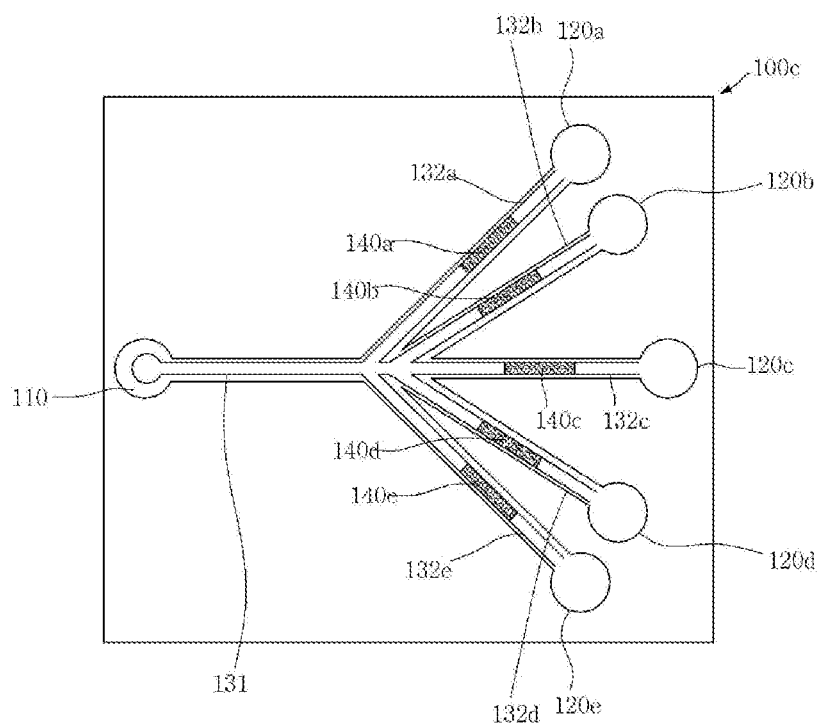

FIG. 7 shows a microfluidic device 100c according to yet another embodiment of the present invention. Referring to FIG. 7, a microchannel 130 of the microfluidic device 100c according to yet may comprise a first flow channel 131 which is connected to a sample chamber 110 and the first flow channel 131 branches off into a plurality of second flow channels 132a, 132b, 132c, 132d, 132e. Further, microbead packings 140a, 140b, 140c, 140d, 140e are arranged in the second flow channel 132a, 132b, 132c, 132d, 132e, respectively.

Here, the microbeads 141 contained in each microbead packings 140a, 140b, 140c, 140d, 140e may have different inner diameter. The probe linkers 143 formed in each microbead 141 may be configured to bond with the same target gene.

In the above arrangement, microbead packings 140a, 140b, 140c, 140d, 140e having small diameter of the microbead 141 may be blocked even when the concentration of target gene in the sample solution is low. The blocking of the microbead packings 140a, 140b, 140c, 140d, 140e depends on the concentration of the target gene in the sample solution and in turn, the blocking of the microbead packings occurs according to the order of the diameter size of the microbead 141. Accordingly, it is possible to evaluate quantitatively the target gene in the sample solution, based on the diameter of the microbead 141 which generates the blocking lastly.

Here, in the embodiment of FIG. 7, for example, a plurality of second flow channels 132a, 132b, 132c, 132d, 132e are connected to each negative pressure chamber 120a, 120b, 120c, 120d, 120e, respectively. Alternatively, it is noted that ends of second flow channels 132a, 132b, 132c, 132d, 132e are merged to be connected to one negative pressure chamber.

Although several embodiments of the present invention are illustrated and explained above, it is obvious that the embodiments can be easily devised by those skilled in the technical idea of the present invention within the scope of the technical idea or spirit included in the specification of the present invention. The scope of the present invention will be determined by attached claims and their equivalents.

INDUSTRIAL APPLICABILITY

The present invention is applied to the field of detecting various pathogenic viruses by the detection of genes.

The invention claimed is:

1. A microfluidic device for detecting a target gene, comprising:
   a sample container containing a sample solution,
   a capillary tube comprising a first end in contact with the sample solution and a second end disposed opposite to the first end, and
   a microbead packing disposed in and between the first end and the second end of the capillary tube,
   wherein the microbead packing comprises:
   a packing tube different from the capillary tube,
   a plurality of microbeads enclosed by the packing tube and in contact with each other to form a plurality of voids between the plurality of microbeads, and
   a plurality of probe linkers disposed on surfaces of the plurality of microbeads,
   wherein the plurality of microbeads are separated from the sample solution by the first end of the capillary tube,
   wherein the sample solution sequentially flows through the first end of the capillary tube, the plurality of microbeads, and the second end of the capillary tube by a capillary phenomenon, and
   wherein the plurality of probe linkers are configured to amplify a target gene in the sample solution by a complementary bonding with the target gene, thereby detecting the target gene.

2. The microfluidic device for detecting a target gene according to claim 1,
   wherein when the sample solution reaches to the plurality of microbeads,
   the plurality of voids are blocked or a distance between the plurality of beads is reduced by the amplification of the target gene by the complementary bonding between the target gene and the probe linker, and
   wherein when the sample solution is further introduced into the sample container, the target gene is detected based on at least one of whether the sample solution flows to the second end of the capillary tube or a final travel distance of the sample solution.

3. The microfluidic device for detecting a target gene according to claim 1,
   wherein the microbead packing comprises a plurality of the packing tube and the plurality of probe linkers in each of the plurality of packing tube are different from each other so as to detect different target genes.

4. The microfluidic device for detecting a target gene according to claim 1,
   wherein an average diameter of the plurality of microbeads is within a range of 0.1 µm to 100 µm, such that the target gene is able to pass through the plurality of voids according to a type of the target gene.

5. The microfluidic device for detecting a target gene according to claim 1,
   wherein the microbead packing comprises meshes disposed at both ends of the packing tube, respectively, to prevent loss of the plurality of microbeads.

6. The microfluidic device for detecting a target gene according to claim 1,
   wherein each of the plurality of the probe linkers comprises a coating part coated on a surface of the plurality of microbeads, a primer attached to the coating part, and a template which complementarily bonds to the primer.

7. The microfluidic device for detecting a target gene according to claim 6,
   wherein the coating part includes one or more selected from a group consisting of 5-hydroxydopamine hydrochloric acid, norepinephrine, epinephrine, pyrogallolamine, DOPA(3,4-Dihydroxyphenylalanine), catechin, tannins, pyrogallol, pyrocatechol, heparin-catechol, chitosan-catechol, poly(ethylene glycol)-catechol, poyl(ethyleneimine)-catechol, poly (methylmethacrylate)-catechol, hyaluronic acid-catechol, polylysine-catechol, and polylysine.

8. The microfluidic device for detecting a target gene according to claim 6,
   wherein the primer includes one or more selected from a group consisting of thiol, amine, hydroxyl, carboxyl, isothiocyanate, NHS ester, aldehyde, epoxide, Carbonate, HOBt ester, Glutaraldehyde, carbamate, imidazole carbamate, maleimide, aziridine, sulfone, vinylsulfone, hydrazine, phenyl azide, benzophenone, anthraquinone, and Diene groups, and wherein a terminal of the primer is modified.

* * * * *